US010584354B2

(12) United States Patent
Wilson

(10) Patent No.: US 10,584,354 B2
(45) Date of Patent: Mar. 10, 2020

(54) METHODS OF GENETICALLY MODIFYING ANIMAL CELLS

(71) Applicant: Wilson Wolf Manufacturing, New Brighton, MN (US)

(72) Inventor: John R. Wilson, New Brighton, MN (US)

(73) Assignee: Wilson Wolf Manufacturing, New Brighton, MN (US)

(*) Notice: Subject to any disclaimer, the term of this patent is extended or adjusted under 35 U.S.C. 154(b) by 0 days.

(21) Appl. No.: 14/494,300

(22) Filed: Sep. 23, 2014

(65) Prior Publication Data
US 2015/0087068 A1 Mar. 26, 2015

Related U.S. Application Data

(60) Provisional application No. 61/881,259, filed on Sep. 23, 2013.

(51) Int. Cl.
C12N 5/071 (2010.01)
C12N 5/00 (2006.01)
C12N 15/00 (2006.01)
C12N 15/86 (2006.01)
C12N 15/87 (2006.01)
C12N 15/85 (2006.01)
C12N 5/0783 (2010.01)
C12N 15/63 (2006.01)

(52) U.S. Cl.
CPC ............ C12N 15/86 (2013.01); C12N 15/85 (2013.01); C12N 15/87 (2013.01); C12N 5/0636 (2013.01); C12N 15/63 (2013.01); C12N 2533/00 (2013.01); C12N 2740/15041 (2013.01)

(58) Field of Classification Search
CPC ... C12N 5/0636; C12N 15/63; C12N 2533/00
USPC ...................... 435/372.3, 395, 455
See application file for complete search history.

(56) References Cited

U.S. PATENT DOCUMENTS

| 7,799,560 | B2 | 9/2010 | Wilson et al. |
| 8,809,044 | B2 | 8/2014 | Wilson |
| 8,956,860 | B2 | 2/2015 | Vera et al. |
| 9,255,243 | B2 | 2/2016 | Wilson et al. |
| 2003/0040104 | A1* | 2/2003 | Barbera-Guillem |
| 2005/0106717 | A1 | 5/2005 | Wilson et al. |
| 2011/0092961 | A1* | 4/2011 | Hyde et al. |
| 2011/0182870 | A1* | 7/2011 | Leen et al. |
| 2013/0102075 | A1* | 4/2013 | Vera et al. |
| 2013/0115617 | A1 | 5/2013 | Wilson |
| 2014/0377739 | A1 | 12/2014 | Welch et al. |

FOREIGN PATENT DOCUMENTS

| EP | 0725134 | 8/1996 |
| WO | WO 95/03408 | 2/1995 |
| WO | WO 9907870 | 2/1999 |
| WO | WO 00/09168 | 2/2000 |
| WO | WO 01/023592 | 4/2001 |
| WO | WO 01/025398 | 4/2001 |
| WO | WO 02/036741 | 5/2002 |
| WO | WO 2005/035728 | 4/2005 |
| WO | WO 2008/148831 | 12/2008 |
| WO | WO 2010/037831 | 4/2010 |
| WO | WO 2011/072088 | 6/2011 |

OTHER PUBLICATIONS

Kohn et al., 2015, U.S. 20150224209 A1, effective filing date, Sep. 14, 2012.*
International Search Report and Written Opinion from related PCT Application PCT/US2014/057030, dated Dec. 29, 2014, 10 pgs.
International Preliminary Report on Patentability from PCT Application PCT/US2014/057030, dated Apr. 7, 2016, 7 pgs.
Lamers C H J et al, "Protocol for gene transduction and expansion of human T lymphocytes for clinical immunogene therapy of cancer", Cancer Gene Therapy, Appleton & Lange, GB, col. 9, 2002, pp. 613-623.
Kalos Michael et al, "T Cells with Chimeric Antigen Receptors Have Potent Antitumor Effects and Can Establish Memory in Patients with Advanced Leukemia", www.ScienceTranslationalMedicine.org, vol. 3, No. 95, Aug. 10, 2011, 11 pgs, downloaded Jan. 16, 2012.
Robert P.T. Somerville et al, "Bioreactors get personal", On Coimmunity, vol. 1, No. 8, Nov. 2012, pp. 1435-1437.
Jin Jianjian et al, "Simplified method of the growth of human tumor infiltrating lymphocytes in gas-permeable flasks to numbers needed for patient treatment", Journal of Immunotherapy, vol. 35, No. 3, Apr. 2012, pp. 283-292.
Vera, Juan F., et al, "Accelerated Production of Antigen-Specific T Cells For Preclinical and Clinical Applications Using Gaspermeable Rapid Expansion Cultureware (G-Rex)", Journal of Immunotherapy, vol. 33, No. 3, Apr. 2010, pp. 305-315.

(Continued)

Primary Examiner — Shin Lin Chen
(74) Attorney, Agent, or Firm — Patterson Thuente Pedersen, P.A.

(57) ABSTRACT

The invention relates to improved methods of genetically modifying animal cells by decreasing the distance between cells and genetic modification agents in order to increase the number of cells modified by a given quantity of genetic modification agents and/or reduce the quantity of genetic modification agents needed to transduce a given number of cells.

7 Claims, 1 Drawing Sheet

(56) References Cited

OTHER PUBLICATIONS

Lapteva, Natalia, et al, "Optimization Manufacture of Virus- and Tumor-Specific T Cells", Stem Cells International, vol. 2011, 2011, pp. 1-8.
Clontech Laboratories, Inc., "Lenti-X™ Lentiviral Expression System User Manual", undated, 27 pgs.
Barbera-Guillem, et al, "OptiCell Concept for Cell Culture Operations", Genetic Engineering, vol. 20, No. 21, Dec. 2000, 4 pgs.
Extended European Search Report from EP Application 14845082.8 dated Jan. 31, 2017, 10 pgs.
Written Opinion from Singapore Application SG 11201602060X, dated Apr. 28, 2017, 7 pgs.
Leda Raptis, "SV40 Protocols, vol. 165", Chapter 8, Humana Press, Inc., 2001, pp. 103-117.
Written Opinion from Singapore Application No. 11201602060X dated Jun. 18, 2018, 5 pgs.
Extended European Search Report from European Application 18215469.0-1120, dated Apr. 3, 2019, 8 pgs.

\* cited by examiner

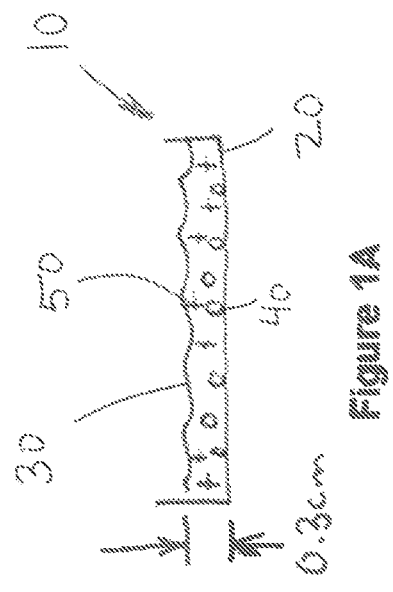
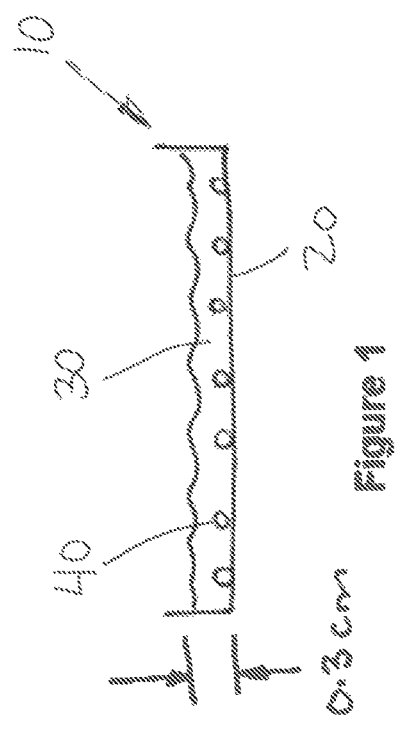
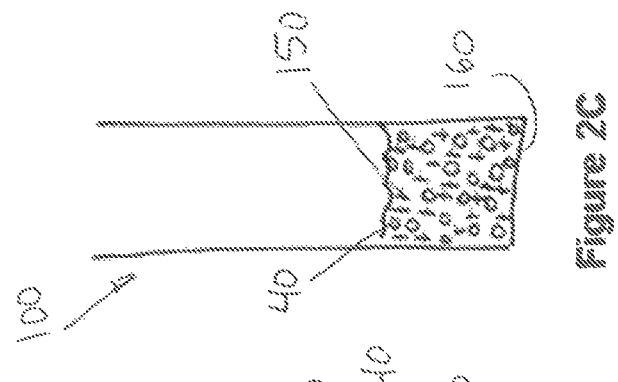
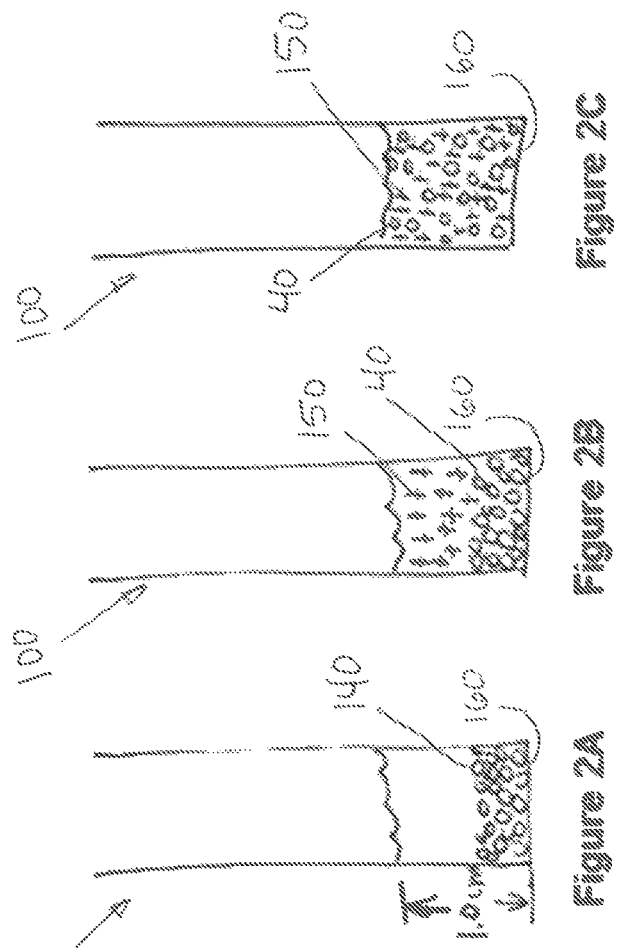
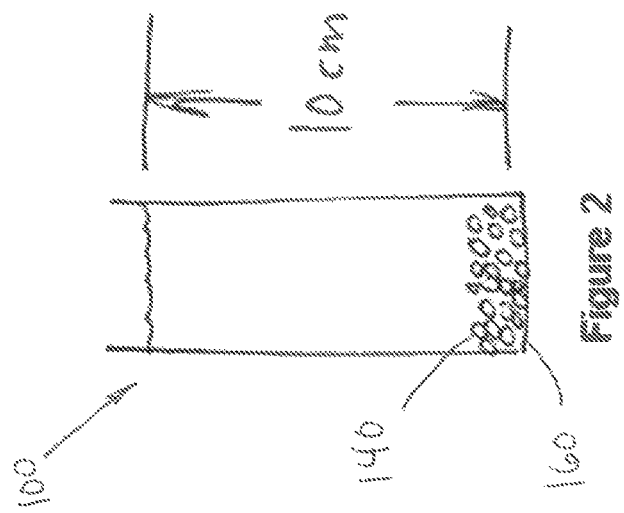

METHODS OF GENETICALLY MODIFYING ANIMAL CELLS

RELATED APPLICATION

The present application claims the benefit of U.S. Provisional Application No. 61/881,259 entitled "IMPROVED METHODS OF CELL TRANSDUCTION", filed Sep. 23, 2013, which is incorporated herein by reference in its entirety.

Each of the applications, patents, and papers cited in this application, and as well as in each document or reference cited in each of the applications, patents, and papers (including during the prosecution of each issued patent; "application cited documents"), pending U.S. patent application Ser. No. 10/961,814 (hereinafter Wilson '814), pending U.S. patent application Ser. No. 13/475,700 (hereinafter Vera '700), pending U.S. patent application Ser. No. 13/493,768 (hereinafter Vera '768), pending U.S. patent application Ser. No. 11/952,848 (hereinafter Wilson '848), pending U.S. patent application Ser. No. 14/313,702 (hereinafter Welch '702) and each of the PCT and foreign applications or patents corresponding to and/or claiming priority from any of these applications and patents, and each of the documents cited or referenced in each of the application cited documents, are hereby expressly incorporated herein.

FIELD OF THE INVENTION

This invention relates to improved methods of genetically modifying animal cells by decreasing the distance between cells and genetic modification agents in order to increase the efficiency of genetic modification and/or reduce use of gene modification agents.

BACKGROUND OF THE INVENTION

Genetically modified cells are commonly referred to as transduced cells after having undergone a process commonly referred to as transduction. Transduction can be undertaken with a variety of techniques to allow gene modifying agents to enter the cell. Such genetic modification agents include the use of viral vectors, electroporation, or chemical reagents that increase cell permeability. Transfection and transformation are also common ways to insert genetic material into a cell.

In the case of viral vectors, there are variations on the types used and such types may include lentivirus, retrovirus, adenovirus, or even nanoengineered substances. In the case of electroporation, cells are exposed to a voltage which allows gene modifying agents such as plasmids to enter the cells. A key challenge is to increase the efficiency by which cells are transduced. An efficiency increase can include an improvement in the number of cells transduced within a given cell population or a reduction in the quantity of genetic modification agents needed to genetically alter a given number of cells within a given population.

Lentivirus provides a good example of the advantages and problems associated with cell transduction. Lentivirus is primarily a research tool used to introduce a gene product into in vitro systems. Large-scale collaborative efforts are underway to use lentiviruses to block the expression of a specific gene using RNA interference technology in high-throughput formats. The expression of short-hairpin RNA (shRNA) reduces the expression of a specific gene, thus allowing researchers to examine the necessity and effects of a given gene in a model system. These studies can be a precursor to the development of novel drugs which aim to block a gene-product to treat diseases.

In the field of T cell therapy, an emerging application is to genetically alter T cells in vitro in order to produce chimeric antigen receptors (CARs) which confer the transduced T cells with specificity, typically the specificity of a monoclonal antibody, to a target antigen. In the this manner, a large number of CAR T cells can be generated for use in T cell therapy. The transduction of CAR T cells may also confer cells with enhancement of activation signal, proliferation, production of cytokines and effector function. There is great potential for this approach to improve patient-specific cancer therapy in a profound way. Following the collection of a patient's T cells, the cells are genetically engineered to express CARs specifically directed towards antigens on the patient's tumor cells, then infused back into the patient, where the CAR T cells recognize and kill cancer cells presenting the target antigen.

The object of this invention is to improve the transduction process by increasing the quantity of cells of any given population size that are transduced upon completion of the process, reduce the quantity of gene modification agents used in the process, and/or reduce the cost and complexity of the process, particularly as it relates to transducing T cells.

A common step in the T cell culture and/or T cell transduction process is to use magnetic beads stained with antibody to select a targeted subpopulation of cells from a larger mixed population. For example, a subpopulation of cells such as stem T cells can be selected from a population of leukocytes. Once a subpopulation of cells that recognize the antibody are bound to beads, the entire population is removed from the device and flows past a magnetic field, whereby beads are trapped by the magnetic field, and the subpopulation of cells attached to the beads are thereby isolated from the main population. A significant process simplification would occur if the need to use a flow system to isolate the subpopulation could be eliminated in favor of conducting the process in a static device does not require liquid to flow.

SUMMARY OF THE INVENTION

Certain embodiments of the present invention are disclosed that improve the process of isolating subpopulations of cells and/or transducing animal cells.

In one embodiment of the present invention, methods are disclosed for reducing the quantity of genetic modification agents needed to transduce cells by a process of putting animal cells and media into a device including a cell growth surface comprised of gas permeable, liquid impermeable material, wherein the animal cells reside at a concentration in the media that exceeds the maximum cell concentration (cells/milliliter) which can be attained by culturing the animal cells in a conventional tissue culture flask using static cell culture methods with media at a height of 0.3 cm, thereby diminishing the distance between any given cell and any given genetic modification agent.

In another embodiment, methods are disclosed for reducing the quantity of genetic modification agents needed to transduce cells by a process of putting animal cells and media into a device including a cell growth surface comprised of gas permeable, liquid impermeable material, wherein the animal cells reside at a concentration in the media that exceeds the maximum cell concentration which can be attained by culturing the animal cells in a conventional tissue culture flask using static cell culture methods with media at a height of 0.3 cm. At this elevated concentration, with a reference point being the initial viability of the cells, genetic modification agents are added into the device, a period of time is allowed for the genetic modification agents to transduce the cells during which cell viability does not decrease below a given percentage of the initial viability.

In another embodiment of the present invention, methods are disclosed for reducing the use of genetic modification agents to transduce animal cells by putting media and animal cells into a device including a cell growth surface comprised of gas permeable material, wherein the animal cells are at a concentration in the media that exceeds the maximum cell concentration which can be attained by culturing said cells in a flask using static cell culture methods with media at a height of 0.3 cm. At this elevated cell concentration, with a reference point being initial glucose concentration of the media, genetic modification agents are added into the device and a period of time is allowed for the genetic modification agents to transduce the cells during which the glucose concentration of the media is not diminished to less than a specified percentage of the initial glucose concentration or a minimum glucose concentration.

In another embodiment of the present invention, methods are disclosed for transducing cells by adding media, animal cells, and genetic modification agents into a device that includes a growth surface comprised of gas permeable, liquid impermeable material, wherein the cells are at a concentration of 3 million to 20 million cells per milliliter of media, and wherein the media is in contact with the gas permeable, liquid impermeable material, and then allowing a period of time during which genetic modification agents act to transduce at least a portion of the cells.

In another embodiment of the present invention, methods are disclosed for transducing cells by increasing the concentration of cells per milliliter of media within a gas permeable cell culture device that contains cells at a first cell concentration, media is at a first media height, and the media is at a first media volume, the first cell concentration being the quantity of cells divided by the first media volume, the first media height being defined by the distance from the uppermost location of the media to the lowest location of the media when the cell growth surface is in a horizontal position, removing a portion of the first media volume from the device leaving a second media volume in the device whereby after removing a portion of the first media volume the cells are at a second cell concentration, the second cell concentration is greater than the first cell concentration, media is a second media height which is defined by the distance from the uppermost location of said media to the lowest location of said media when the cell growth surface is in a horizontal position, and adding genetic modification agents into the device, allowing a period of time whereby the genetic modification agents act to transduce at least a portion of the cells. A subsequent step can be performed to expand the population size of the transduced cells by adding a volume of media into the device and allowing a period of time for cells to be cultured with the media when the device is oriented in a position such that at least a portion of the cells reside upon the cell growth surface and the cell growth surface is oriented in a horizontal position and ambient gas suitable for cell culture is in contact with the gas permeable liquid impermeable material.

In another embodiment of the invention a method of isolating a subpopulation of cells from a larger population is disclosed in which a population of cells, media, and coated magnetic beads are added into a device comprising gas permeable, liquid impermeable material, a period of time is allowed for a subpopulation of cells to attach to the magnetic beads, the beads within the device are exposed to a magnetic field, and media and a population of cells are removed while magnetic beads remain in the device due to the magnetic field, thereby separating a subpopulation of cells from a larger population of cells.

In another embodiment of the invention a method of isolating a subpopulation of cells from a larger population is disclosed in which a population of cells, media, and coated magnetic beads are added into a device comprising gas permeable, liquid impermeable material, a period of time is allowed for a subpopulation of cells to attach to the magnetic beads, the beads within the device are exposed to a magnetic field, and media and a population of cells are removed while magnetic beads remain in the device due to the magnetic field, thereby separating a subpopulation of cells from a larger population of cells. Cells in the device are then transduced using any of the methods described herein.

BRIEF DESCRIPTION OF THE DRAWINGS

FIG. 1 shows a cross-section of a non gas permeable cell culture device that contains cells and media.

FIG. 1A shows a cross-section of a non gas permeable cell culture device that contains cells, media, and genetic modification agents.

FIG. 2 shows a cross-section of a gas permeable cell culture device that contains cells and media.

FIG. 2A shows a cross-section of a gas permeable cell culture device that contains cells and media.

FIG. 2B shows a cross-section of a gas permeable cell culture device that contains cells, media, and genetic modification agents.

FIG. 2C shows a cross-section of a gas permeable cell culture device that contains cells, media, and genetic modification agents.

DETAILED DESCRIPTION OF THE INVENTION

One embodiment of the present invention that is advantageous for genetically modifying animal cells is best understood by comparing a conventional process shown in FIG. 1 and FIG. 1A with the novel process shown in FIG. 2, FIG. 2A, FIG. 2B, and FIG. 2C. FIG. 1 shows a cross-sectional view of conventional static cell culture device 10 such as a flask, which has cell growth surface 20 that is not gas permeable. In this example, media 30 resides at a typical height of 0.3 cm and above a 100 $cm^2$ cell growth surface. Thus, 30 ml of media resides above the 100 $cm^2$ cell growth surface, giving a media to cell growth surface area ratio of 0.3 $ml/cm^2$. In accordance with conventional wisdom, cells 40 (shown as circles) reside at a typical concentration no greater than 2 million cells per ml, and therefore at most 60 million cells reside in the device (i.e. 2 million cells per ml times 30 ml of media). At a device cell growth surface area of 100 $cm^2$, cells therefore once cells have gravitated to the cell growth surface they reside at a surface density of 0.6 million cells per $cm^2$ (i.e. 60 million cells divided by 100 $cm^2$ of surface area). FIG. 2 shows a cross-sectional view of gas permeable device 100, for example such as described within Wilson '814, Vera '700, Vera '768, Wilson '848, Welch '702 and the commercially available G-Rex® devices, which advocate and/or allow media to reside at a height well beyond conventional devices and allow cells to reside at a higher surface density than conventional culture devices. In this example, cells 40 (shown as circles) are in a state of static culture and have gravitated to the bottom of the device, which is comprised of gas permeable, liquid impermeable cell growth surface 160. Media 130 resides at a height of 10 cm above gas permeable, liquid impermeable cell growth surface 160 that has a cell growth surface area of 100 cm$^2$, giving a media volume of 1000 ml and a media volume to cell growth surface area ratio of 10 ml/cm$^2$. At a cell concentration of 2 million cells per ml, 2 billion cells are present in the device. The cells reside at a surface density of 20 million cells per cm$^2$, over 33 times that in the conventional flask of FIG. 1 (i.e. 20 million cells per cm$^2$ divided by 0.6 million cells per cm$^2$), despite being at an equivalent concentration of 2 million cells per milliliter.

The following description shows how the distance between gene modifying agents and cells can be reduced in the gas permeable device of FIG. 2, enhancing transduction efficiency.

FIG. 1A shows the conventional flask device cross-section of FIG. 1 after genetic modification agents 50, shown with plus marks (+), have been added to the media. In this example, the quantity of genetic modification agents is at a one to one ratio with the quantity of cells. Skilled artisans are encouraged to recognize the ratio can be any desired, not just the one to one ratio depicted in this illustrative embodiment. The genetic modification agents are at a lower specific gravity than that of cells, and at a specific gravity that prevents them from gravitating to the bottom of the device as the cells do. FIG. 2A shows the cross-sectional view of the gas permeable device of FIG. 2 after the media has been reduced from its first height of 10 cm to a second height of 1 cm, thereby increasing cell concentration from its first cell concentration of 2 million per ml to its second cell concentration of 20 million per ml. Stated differently, the cell concentration has been increased by a factor of 10 (i.e. 2 million per ml to 20 million per ml). Importantly, this is 10 times greater than the 2 million per ml concentration of the conventional device. FIG. 2B shows the gas permeable device of FIG. 2A after genetic modification agents 150, shown as plus signs (+), have been added to the media. In this example, the quantity of genetic modification agents is at a one to one ratio with the quantity of cells. In this example, since the cells/ml are 10 times as concentrated in the gas permeable device of FIG. 2 as in the conventional flask device of FIG. 1, the ability to decrease the distance between any given genetic modification agent and any given cell in the gas permeable device relative to the conventional flask device is proportional to the increase in cell concentration as media height is reduced. Stated differently, the distance decreases between genetic modification agents and cells as the height of media decreases. Thus, any given genetic modification agent is more likely to make contact with a cell by Brownian motion. Increased frequency of contact increases the probability of any given genetic transduction agent transducing a cell.

To further increase transduction efficiency, it may be advantageous to move the cells out of their resting position, which is a result of the static state of the media and gravity acting on the cells to move them to the bottom of the device. FIG. 2C shows the cells in a state of distribution throughout the media, which can be accomplished by moving the media out of a static state and into a non-static state of forced motion within the device. This may be as simple as moving the device by hand, such as by shaking or swirling the device, but preferably for consistency may be done by imparting motion to the device or to the media by use of a any number of more controlled mechanisms including use of an orbital shaker, a shaker plate, or any mechanism or method to vibrate, mix, or agitate the media. Stated differently, by putting the media into a state of forced motion, as opposed to a static state that allows cells to gravitate to the device bottom, cells are moved from the bottom and into a state of distribution throughout the media. In the state of distribution throughout the media, cells are even more likely to make contact with genetic modification agents.

In the gas permeable device, after a period of time wherein the cells are in their increased concentration in the media and are in the presence of genetic modification agents, the cell population can be moved from a state of transduction to a state of cell culture. Thus, media can be restored to a greater height or the cells can be washed of the genetic modification agents and re-suspended in one or more gas permeable devices for population expansion.

The advantages of the transduction method of the present invention relative to the conventional method of transduction are numerous. The reduction in distance between cells and genetic modification agents increases the probability of contact over any given time. With increased contact, an increase in the proportion of cells that are genetically altered is possible. Also, to get an equal proportion of the population of cells to be genetically altered when compared to the conventional process, a smaller quantity of genetic modification agents can be used. Furthermore, the duration by which the cell transduction process is undertaken can be reduced. Skilled artisans are encouraged to recognize that preferably the gas permeable device walls are rigid to ensure that cells are not disturbed when moving the device, as may be the case if the device is handled and moved when media is reduced from its first height to its second height. So doing could move the cells out of their resting position on the cell growth surface and into the media, whereby cells could be lost during media height reduction. Stated differently, cells are preferably in a resting position upon a surface of the device when media is removed. The gas permeable device is preferably not a traditional cell culture bag, as cell culture bags are not rigid and cells are moved from a resting state upon the wall of the bag to a state of distribution within the media when bags are handled.

The duration at which cells in the gas permeable device can be sustained at elevated concentration is dependent on cell metabolism. Based on knowledge gained in culture experiments with T cells, when cell concentration is increased by up to 4 million cells per ml by reducing media height (i.e. volume) when the cells are resting on the cell growth surface, the duration of time prior to completion of the genetic modification process is preferably not longer than 24 hours. In other words, media height is preferably is not in its decreased state for a period beyond 48 hours after it has been reduced from its first height to its second height. When, by reducing media height (i.e. volume) when the cells are resting on the cell growth surface, cell concentration is increased beyond 4 million cells per ml and up to 8 million per ml, the duration of time prior to completion of the genetic modification process preferably is not beyond 24 hours. When, by reducing media height (i.e. volume) when the cells are resting on the cell growth surface, cell concentration is increased beyond 8 million cells per ml and up to 16 million per ml, the duration of time prior to completion of the genetic modification process is preferably not longer than 12 hours. When, by reducing media height (i.e. volume) when the cells are resting on the cell growth surface, cell concentration is increased beyond 16 million cells per ml and up to 32 million per ml, the duration of time prior to completion of the genetic modification process is preferably not longer than 6 hours.

The prior example shows how efficiency can be increased in a gas permeable device wherein the cell growth surface is comprised of gas permeable, liquid impermeable material by temporarily increasing cell concentration when the ratio of the quantity of genetic modification agents to cells is the same as that of conventional non gas permeable static devices. It is also possible to use this method to reduce the number of genetic modification agents needed to achieve the same transduction efficiency that conventional devices allow. In this case, transduction efficiency refers to the percentage of a cell population that is genetically modified. In practice for example, to achieve the same transduction efficiency as obtained in a traditional non gas permeable static cell culture device such as a flask, one could reduce the ratio of genetic modification agents to cells within a gas permeable device in inverse proportion to that required for conventional devices. For example, in the case where infectious agents such as viral vectors are the genetic modification agents, the ratio of infectious agents to infectious targets (also commonly referred to as the multiplicity of infection or MOI) could be reduced by the ratio of the cell concentration in conventional static devices such as flasks to the cell concentration in static gas permeable devices such as G-Rex® or any of the gas permeable devices described in the cited related applications. For example, in the previous discussion related to FIG. 1 through FIG. 2C, where cells in the gas permeable device are 10 times the concentration of the flask, if the genetic modification agents where viral vectors, the number viral vectors such as lentivirus could be reduced. This could be useful in reducing the cost of the process. For example, if the MOI where 5 in the flask, the MOI could be less than 5 in the gas permeable device and the transduction efficiency may not be diminished.

One need not perform a first step of culturing the cells to high surface density (i.e. cells/cm$^2$) and then reducing media height to increase cell concentration for the invention to be applied. One could simply move cells and media into a device with a cell growth surface comprised of gas permeable material in a manner such that the cell concentration exceeds that of conventional culture devices such as a flask and the transduction processes flasks rely upon. Preferably, cell concentration is beyond 2 million cells/ml including 3, 4, 5, 6, 7, 8, 9, 10, 11, 12, 13, 14, 15, 16, 17, 18, 19, 20, 21, 22, 23, 24, 25, 26, 27, 28, 29, 30, and beyond. Skilled artisans are encouraged to recognize the concentration need not be the exact integer, such as 5, but can be any number, preferably at a concentration range greater than 2 million cells/ml. Preferably, cell concentration is beyond 2 million cells/ml and not beyond 30 million cells/ml, more preferably beyond 3 million cells/ml and up to 20 million cells/ml, even more preferably beyond 4 million cells/ml up to 20 million cells/ml, and most preferably beyond 5 million cells/ml up to 20 million cells/ml. However, artisans should recognize that ranges are not limited and for example a range of 10 million cells/ml to 20 million cells/ml is also within the scope of this invention. The goal is to increase the number of cell targets per milliliter of media relative to prior transduction methods carried out in a cell culture device, thereby decreasing the distance between any given cell and any given transduction agent and given cell.

A key aspect is to allow the cells to obtain oxygen via a surface other than the gas-media interface at the upper surface of the media. Preferably cells obtain oxygen via the surface upon which cells reside. With cells residing upon a gas permeable, liquid impermeable cell growth surface, ambient gas will be in contact with the opposite side of the gas permeable surface. The ambient gas need only be in passive contact with the gas permeable material. Stated differently, it is advantageous if cells do not rely solely upon a gas-media interface for oxygen delivery. In this manner, cells obtain oxygen independent of how far they are from the gas-liquid interface, if one exists. It may be also advantageous to structure a device and process where the gas-liquid interface is eliminated altogether so long as a wall is gas permeable, preferable the wall in which cells contact.

The duration at which the transduction process can occur in the present invention is limited by the cell concentration, which will place a metabolic demand on the media in proportion to the increase in cell concentration. As one example, T cells have been cultured in G-Rex® gas permeable devices beginning at concentrations of about 500,000 cells per cm$^2$, at a medium height of 11 cm (a medium volume to surface area ratio of 11 ml/cm$^2$) and the culture was allowed to expand in population size for time period up to 11 days without feeding until cells reached a peak concentration of about 3 million per ml. At that point in time, viability did not diminish beyond about 3-5% for up to an additional 2 days. Thus, skilled artisans are encouraged to recognize that cells consumed nutrients out of the media for a long period of time as the population of cells increased. Therefore, cells can be expected to reside at very high concentration in the media, well beyond 3 million per ml for at least a day, without substantial loss in viability. Since many transduction protocols can be completed within a day, and many within a few hours, there is an opportunity to transduce a population of cells that are at cell concentrations that exceed those attainable using 1) conventional static culture methods and static cell culture devices such as those of flasks, or 2) using high surface density static cell culture methods with static gas permeable cell culture devices such as those of Wilson '814, Wilson '848, Wilson 700, Vera '768, Welch '702 and/or G-Rex®™. One example of how to determine the appropriate cell concentration and conduct transduction is described below for a transduction process in which it is desirable to complete the process within 24 hours. Such a process would be comprised of:

Step A. Allowing cells to reside at cell concentration that exceeds that of a flask and preferably beyond about 2 million per ml, such as those previously described including 3 million per ml, 4 million per ml, 5 million per ml, 6 million per ml and so forth. Measuring glucose depletion and determining the amount of time until the glucose remains above about 50 mg/dl and more preferably at or above 80 mg/dl and most preferably at or above 100 mg/dl. Alternatively, one can measure initial viability of the cell population and determine the amount of time until the initial viability is diminished by some percentage, preferably no more than 20%, more preferably no more than 10%, even more preferably no more than 5%, and most preferably not at all. Thus, selecting a cell concentration at the onset of the transduction process that conforms to the preferable glucose and/or viability conditions over a period of time that does not exceed 24 hours is preferred. Skilled artisans are encouraged to recognize that in the preferred state any starting cell concentration is acceptable, so long as the preferred glucose depletion and/or preferred viability values are maintained throughout the transduction time period. Thus, there will be a trade-off between starting cell concentration and duration.

Step B. Adding genetic modification agents to the media in which cells reside. The ratio of the quantity genetic modification agents to the quantity of cells could be any ratio that is found to increase transduction efficiency relative to transduction conducted within the conventional cell concentration limits, such as the 2 million cells per ml limit typical of flasks and other static non-gas permeable culture devices and processes. Preferably, the ratio is 1 or more, more preferably from 1 to 5, and most preferably from 1 to 2. By elevating the cell concentration and providing a ratio of 1, an increase in the percentage of cells that become transduced is expected as the cells and transduction agents are closer to each other than when at conventional cell concentrations. If the cost or availability of transduction agent is a concern, the elevated cell concentration and resulting closer distance between cells and genetic modification agents relative to conventional methods allows the ratio to be reduced below 1 with an expectation that a similar percentage of cells will be transduced as that of conventional methods at a ratio of 1. Whether the goal is to increase the number of cells transduced or to reduce the use of genetic modification agents, the process need not require forced mixing of the genetic modification agents with cells, but could do so if it increases the number of cells transuded or minimizes use of genetic modification agents.

A key advantage of gas permeable device is the ability to allow media to reside at unconventional media height, while cells obtain access to oxygen travelling through the device walls, preferably the cell growth surface upon which cells reside. Preferably, cells have gravitated to a gas permeable, liquid impermeable cell growth surface that is in contact with ambient gas. When using gas permeable material, liquid impermeable, non porous silicone is preferred due to its high oxygen transmission capacity. A cell population can be expanded from a small quantity to a large quantity using devices and methods of Wilson '814, Vera '700, Vera '768, Vera '700, and/or Wilson '848. Thereafter, cells can be concentrated using methods and devices of Vera '701 and/or Welch '702. However, unlike the methods of Vera '700 in which cells are immediately removed from the device after removing media to place cells at unconventionally high concentration that is beyond 2 million cells per milliliter of media within the device, the cells can remain in the device and the device can also act as the transduction device while a next step of transduction occurs. Alternatively, cells can be moved from any device in which they were present and added into the gas permeable device whereby a step of transduction at high cell concentration can occur. The key advantage is the ability to create a high cell concentration, preferably in the ranges previously described.

Skilled artisans are encouraged to recognize that the processes of increasing transduction efficiency can be embodied in any number of the steps including:

a) adding animal cells to a device with a gas permeable liquid impermeable growth surface, b) allowing the cells to gravitate to the growth surface under a first height of media at a first cell concentration, c) optionally allowing the cells to expand in quantity to a second cell concentration d) reducing the media from a first height to a lower, second height, thereby creating a third cell concentration, the third cell concentration exceeding the first cell concentration and the second cell concentration, d) adding a quantity of genetic modification agents preferably at any of the ratios to cell quantity previously described, e) allowing a period of time for the transfection preferably in which the cell viability and or glucose concentration stays within preferred limits, f) adding more medium to raise the height of medium to a new level, g) culturing the cells to expand the quantity of the transduced cell population.

Skilled artisans are encouraged to recognize the cell need not be cultured. For example, processes of increasing transduction efficiency can be as simple as:

a) adding animal cells and media into a device with a gas permeable liquid impermeable growth surface, b) allowing the cells to gravitate to the growth surface under a first height of media at a first cell concentration that exceeds that possible when culturing the animal cells in static tissue culture flasks, or optionally just choosing a cell concentration within the preferred ranges previously identified, c) adding a quantity of genetic modification agents preferably at any of the ratios to cell quantity previously described, d) allowing a period of time for the transfection preferably in which the cell viability and or glucose concentration stays within preferred limits.

A common step in the T cell culture and/or T cell transduction process is to use coated magnetic beads to select a targeted subpopulation of cells from a larger mixed population of cells. The coating is typically antibody that binds with the cells. After allowing a period of time for a targeted subpopulation of cells to attach with the beads, the entire cell population and media flow past a magnetic field whereby beads are trapped by the magnetic field and the subpopulation of cells attached to the beads are thereby isolated from the mixed population. A significant process simplification would occur if the need to use a flow system to isolate the subpopulation could be eliminated in favor of conducting the process in a static device. An even greater process simplification would occur if the static device were capable of transducing the subpopulation targeted by the coated beads in ways that are more efficient than conventional methods.

An improved process is attained by use of a gas permeable device, configured in any manner previously described, including those in any of the cited related applications, into which a mixed population of cells, media, and coated beads are added. Beads and cells can gravitate to the gas permeable material as with static culture methods, or if one chooses to force the beads and cells to move with the intent of increasing contact, the media in the device can be placed into a non-static state by conventional methods of mixing the media, such as by shaking, or stirring the device in order to increase cell contact with the beads. In any event, after a given period of time in which cells and beads attach to one another, the beads are exposed to a magnetic field, trapping the beads within the device. Then media and cells that have not attached to the beads are removed, leaving a desired subpopulation of cells within the device.

In the case in which the subpopulation of cells is one of positive selection (i.e. the cells attached to beads are the desired subpopulation), they can be then transduced by any of the previously described methods. In the case where the subpopulation of cells is one of negative selection (i.e. the cells attached to beads are not the desired subpopulation), the removed population (i.e. the population that has not attached to beads) can be transduced by any of any of the previously described methods. In the case of negative selection in which the same device is to be used for transduction, after removing the population that has not attached to beads the magnetic field can be terminated, beads can be removed from the device, and the population of cells that did not attach to beads can be added back into the device, whereby that population can be transduced by any of any of the previously described methods. An additional step to culture the cells can be undertaken using any of the described methods of the present invention inclusive of the cited related patents, followed by optionally separating the beads from the cells if so desired.

In a preferred embodiment, beads are coated with antibodies that bind with stem T cells such as such as CD45RA, C62L, and CCR7. In another preferred embodiment, beads are coated with antibodies that bind with regulatory T cells such as $CD4^+$, CD25 bright, and CD127 low. Preferably the mixed population of cells is a population of leukocytes.

In a preferred embodiment the magnetic field created by a magnet in contact with a gas permeable material support which is in contact with a gas permeable cell growth surface. Preferably the surface of the magnet is parallel to the gas permeable cell growth surface. More preferably a surface of the magnet is parallel to the cell growth surface and within 0.5 inches, even more preferable within 0.3 inches, and most preferable within 0.2 inches.

The term transduction is not limiting as used herein and is broadly defined to include any form of genetic modification of cells that relies on genetic modification agents being in contact with cells. Preferably, the gas permeable device is not compartmentalized by a semi-permeable membrane, such as a dialysis membrane. Stated differently, the device preferably does not have a separate compartment in which cells reside that is bounded at least in part by a semi-permeable membrane. Preferably the bottom of the device is comprised of a gas permeable cell growth surface that is in a planar and horizontal state when the media height is being reduced and/or animal cells are being cultured. Preferably the gas permeable material is in contact with media throughout the cell culture process and/or the transduction process. Preferably, the gas permeable material is in contact with ambient gas and a gas permeable material support such as that described in Wilson '814 for example in paragraph [0136].

Skilled artisans are also encouraged to recognize that media height can be height that is far greater than conventional wisdom as described in Wilson '814, for example in EXAMPLE 1 and TABLE 1. Skilled artisans are also encouraged to recognize that EXAMPLE 1 and TABLE 1 of Wilson '814 show that media height can be any height beyond conventional wisdom of 2.0 cm, including height at not only 3.02 cm, 5.09 cm, 10.20 cm, 15.31 cm, and 20.39 cm, but at any intermediary height such as 2.5 cm, 3.03 cm, 4.0 cm, 15.32 cm and the like since advantages continued to accrue as media increased in accordance with EXAMPLE 1 and TABLE 1. The benefits of elevated media height are further described in Vera '700 as described in EXAMPLE 9, EXAMPLE 11, and in numerous other examples in Vera '700. From Vera '700, one can ascertain for example that expanding cells from a cell surface density of 1,000,000 cells/$cm^2$ with a media height of 10 cm and a cell concentration of 100,000 cells/ml is an efficient process. Expanding cells from a cell surface density of 3,000,000 cells/$cm^2$ with a media height of 10 cm and a cell concentration of 300,000 cells/ml may be a good choice when patient to patient variability in expansion rate is great and there is a desire to create a surface density higher than conventional methods to help ensure cells are in close enough communication for the onset of expansion. However, low cell surface density has also been shown beneficial in Vera '700.

Skilled artisans should also recognize that were the instant invention identifies ranges, and number within the range is included. This also applies to the cited related applications, and in particular Wilson '814 and Vera '700. Further skilled artisans should know that none of the cell culture experiments relied on fibronectin, a fragment thereof, or a mixture thereof in Vera '700.

Skilled artisans should also recognize that the benefits obtained by expanding cells from any number of unconventionally low cell surface densities to any number of unconventionally high cell surface densities, as described in described in Vera '700. For example, Vera '700 described numerous examples including CAR T expansion in EXAMPLE 14, which can be beneficial in the present invention when transducing and expanding a population of CAR T cells.

Skilled artisans are also encouraged to recognize that methods of reducing media height described in Vera '700, for example surrounding FIG. 22A, FIG. 22B, FIG. 22C, and FIG. 22C of Vera '700 and associated text can be beneficial to reducing media height in the present invention.

Those skilled in the art will recognize that numerous modifications can be made to this disclosure without departing from the spirit of the inventions described herein. Therefore, it is not intended to limit the breadth of the invention to embodiments and examples described. Rather, the scope of the invention is to be interpreted by the appended claims and their equivalents.

The invention claimed is:

1. A method of transducing and culturing T cells comprising:
    adding media, T cells, and genetic modification agents into a device that includes a horizontal growth surface comprised of a gas permeable, liquid impermeable material, said T cells are at a first concentration of 4 million to 20 million cells per milliliter of media, said T cells in contact with said gas permeable, liquid impermeable material, said gas permeable, liquid impermeable material being in a horizontal position, and
    allowing a period of time whereby said genetic modification agents act to transduce at least a portion of said cells, and
    adding media to said device, thereby reducing the concentration of T cells in the media to a second concentration and allowing at least 4 and up to 11 days for the T cells to increase in quantity without adding media.

2. The method of claim 1 wherein said T cells are at a first concentration of 5 million to 20 million cells per milliliter of media.

3. The method of claim 1 wherein said T cells are at a first concentration of 6 million to 20 million cells per milliliter of media.

4. The method of claim 1 wherein the media in the device is not in a static state during at least a portion of the period of time whereby said genetic modification agents act to transducer at least a portion of said T cells.

5. The method of claim 1 wherein said genetic modification agent is comprised of lentivirus.

6. The method of claim 1 wherein said gas permeable, liquid impermeable material is in contact with a gas permeable material support and is in contact with ambient gas.

7. The method of claim 1 wherein the ratio of the number of genetic modification agents to the quantity of T cells added to the device is not greater than 2.

* * * * *